United States Patent [19]

Sakai et al.

[11] Patent Number: 5,772,602
[45] Date of Patent: Jun. 30, 1998

[54] NONINVASIVE BLOOD PRESSURE MEASURING DEVICE AND METHOD

[75] Inventors: Yoshio Sakai; Toshichika Kaji, both of Tokyo, Japan

[73] Assignee: Nihon Kohden Corporation, Tokyo, Japan

[21] Appl. No.: 747,896

[22] Filed: Nov. 13, 1996

[30] Foreign Application Priority Data

Nov. 14, 1995 [JP] Japan .................................. 7-295262
Oct. 17, 1996 [JP] Japan .................................. 8-274329

[51] Int. Cl.[6] .............................................. A61N 5/022
[52] U.S. Cl. ......................................................... 600/495
[58] Field of Search ................................. 128/672, 680, 128/681, 682, 687; 600/485, 493, 494, 495, 500

[56] References Cited

U.S. PATENT DOCUMENTS

| 4,349,034 | 9/1982 | Ramsey, III | 128/681 |
| 5,099,853 | 3/1992 | Uemura et al. | 128/681 |
| 5,139,026 | 8/1992 | Niwa | 128/672 |
| 5,606,977 | 3/1997 | Ramsey, III et al. | 128/681 |

*Primary Examiner*—William E. Kamm
*Attorney, Agent, or Firm*—Sughrue, Mion, Zinn, Macpeak & Seas, PLLC

[57] ABSTRACT

A CPU 9 controls an air supplying/discharging device to set a pressure of air within a-cuff to 60 mmHg for 60 seconds before making a blood pressure measurement, detects pulse waves of the cuff pressure for such period of time, and calculates a degree of stability of the detected pulse waves. When a blood pressure measurement is made, the CPU reduces the cuff pressure by a step pressure reducing operation whose step duration corresponds to the calculated degree of stability.

32 Claims, 3 Drawing Sheets

FIG. 1

END OF BLOOD PRESSURE MEASUREMENT

| STAGE CLASSIFIED | CONDITION |
|---|---|
| STAGE 1 | PRsd% < 40% |
| STAGE 2 | 40% ≦ PRsd% < 80% |
| STAGE 3 | 80% ≦ PRsd% |
| STAGE 4 | NUMBER OF DETECTED PULSE WAVE |

NONINVASIVE BLOOD PRESSURE MEASURING DEVICE AND METHOD

BACKGROUND OF THE INVENTION

1. Field of the invention

The invention relates to a vibration-resistant noninvasive blood pressure measuring device method.

2. Related art

When blood pressure is measured with a noninvasive blood pressure measuring device, e.g., in an ambulance, correct measurement cannot be made because the measurement is affected by vibration. There have not yet been available noninvasive blood pressure measuring devices that are designed to adequately remove vibration-induced noise, taking such vibration into account.

Since conventional noninvasive blood pressure measuring devices erroneously pick up a vibration-induced noise as a pulse wave of the blood pressure, correct blood pressure measurement cannot be made.

SUMMARY OF THE INVENTION

The invention has been made in view of the aforementioned shortcoming. The object of the invention is therefore to provide a noninvasive blood pressure measuring method and corresponding device that is less affected by vibration-induced noise.

According to an aspect of the present invention, there is provided a noninvasive blood pressure measuring device having a cuff to be wrapped around a body and measuring blood pressure based on a pressure of a gas within the cuff, including: a gas supplying/discharging means for supplying and discharging the gas with respect to the cuff; a first cuff pressure control means for controlling the gas supplying/discharging means so that the pressure of the gas within the cuff reaches a first pressure; a stability detecting means for detecting a pulse wave in the pressure while the pressure of the gas within the cuff is maintained at the first pressure by the first cuff pressure control means and for detecting a degree of stability of the detected pulse wave; a judging means for judging whether or not a predetermined pressure reducing operation is performed based on the degree of stability detected by the stability detecting means; a second cuff pressure control means for controlling the gas supplying/discharging means so that after the pressure of the gas within the cuff has increased to a second pressure, the predetermined pressure reducing operation is performed to the pressure of the gas within the cuff when the judging means has judged to perform the predetermined pressure reducing operation; and a blood pressure value determining means for detecting a pulse wave in the pressure while the predetermined pressure reducing operation is performed to the pressure of the gas within the cuff by the second cuff pressure control means and for determining a blood pressure value based on the detected pulse wave.

According to another aspect of the present invention, there is provided a noninvasive blood pressure measuring device wherein the judging means determines a single type of predetermined pressure reducing operation out of a plurality of types of predetermined pressure reducing operations in accordance with the degree of stability of the pulse wave detected by the stability detecting means; and the second cuff pressure control means controls the gas supplying/discharging means so that the single type of predetermined pressure reducing operation determined by the judging means is performed to the pressure of the gas within the cuff.

Another aspect of the present invention, there is provided a noninvasive blood pressure measuring method and corresponding device having a cuff to be wrapped around a body and measuring blood pressure based on a pressure of a gas within the cuff, including: a gas supplying/discharging means for supplying and discharging the gas with respect to the cuff; a first cuff pressure control means for controlling the gas supplying/discharging means so that the pressure of the gas within the cuff reaches a first pressure; a stability detecting means for detecting a pulse wave in the pressure while the pressure of the gas within the cuff is maintained at the first pressure by the first cuff pressure control means and for detecting a degree of stability of the detected pulse wave; a judging means for selecting the a of predetermined pressure reducing operation from the plurality of types of predetermined pressure reducing operations in accordance with the degree of stability detected by the stability detecting means; a stability analyzing means for analyzing a degree of stability of a pulse wave in the pressure of the gas within the cuff while any one of the plurality of predetermined pressure reducing operations is performed, and for newly selecting a predetermined pressure reducing operation out of the plurality of predetermined pressure reducing operations based on the analyzed degree of stability; a second cuff pressure control means for controlling the gas supplying/discharging means so that after the pressure of the gas within the cuff has increased to a second pressure, the predetermined pressure reducing operation selected by the judging means is performed to the pressure of the gas within the cuff and for controlling the gas supplying/discharging means so that the predetermined pressure reducing operation selected by the stability analyzing means is performed to the pressure of the gas within the cuff thereafter; and a blood pressure value determining means for detecting a pulse wave in the pressure while the predetermined pressure reducing operation is performed to the pressure of the gas within the cuff by the second cuff pressure control means and for determining a blood pressure value based on detected pulse wave.

According to the present invention, the predetermined pressure reducing operations are predetermined step pressure reducing operations.

DETAILED DESCRIPTION OF THE PREFERRED EMBODIMENTS

Figure 1:
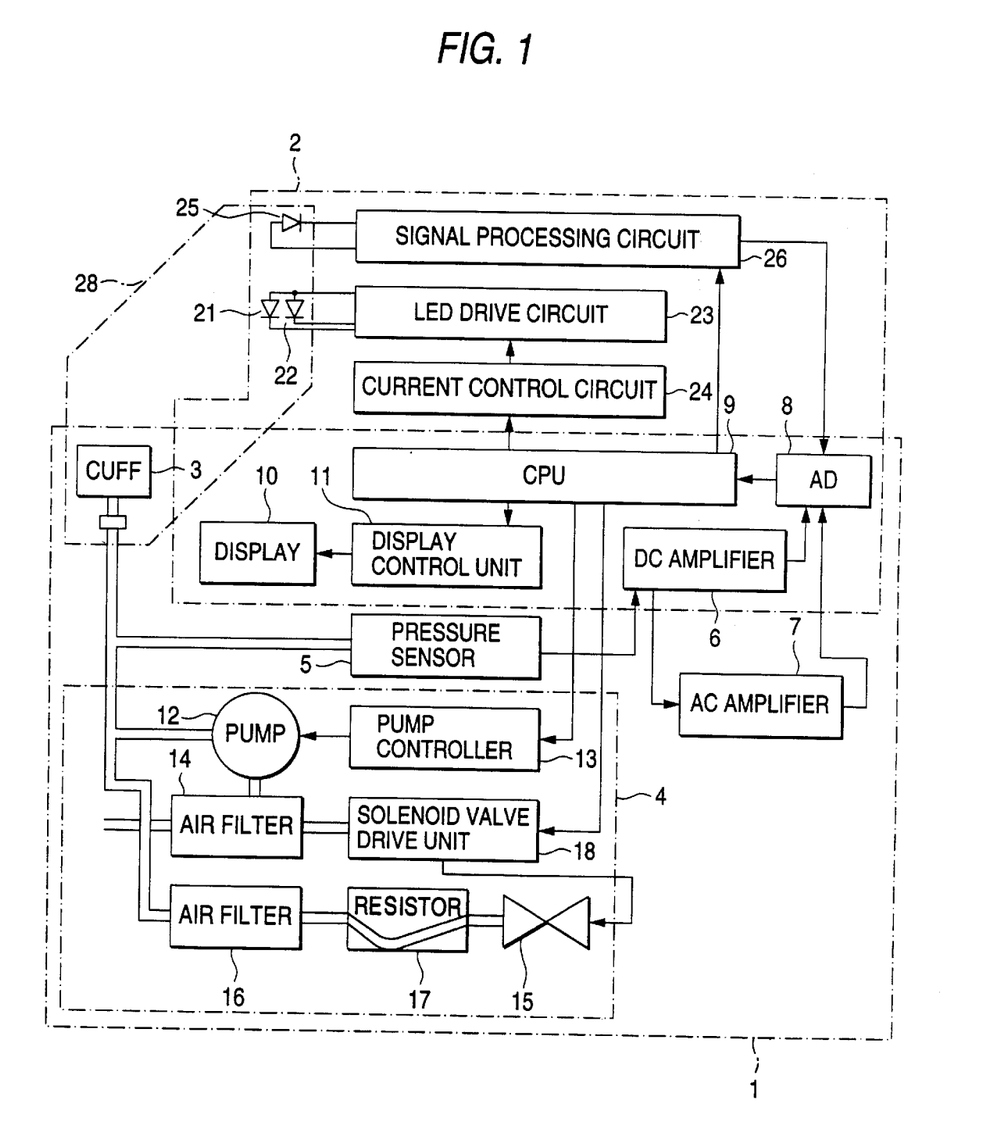
FIG. 1 is a block diagram showing an overall configuration of an apparatus, which is a mode of embodiment of the invention.

One mode of embodiment of the invention will now be described. FIG. 1 is a block diagram showing an overall configuration of the mode of embodiment of the invention. A noninvasive blood pressure measuring device, which is the embodiment of the invention, has a blood pressure measuring section 1 and an arterial blood oxygen saturation degree measuring section 2. The blood pressure measuring section 1 includes: a cuff 3 that is wrapped around a finger of a subject; an air supplying/discharging means 4 that supplies and discharges air to and from the cuff 3; a pressure sensor 5 that detects the pressure of the air within the cuff 3;

a dc amplifier 6 that detects a cuff pressure from the pressure detected by the pressure sensor 5; an ac amplifier 7 that detects a pulse wave from the pressure detected by the pressure sensor 5; an A/D converter 8 that converts the outputs of the dc amplifier 6 and ac amplifier 7 from analog values to digital values; a CPU (central processing unit) 9 that not only controls the air supplying/discharging means 4 but also processes data delivered from the A/D converter 8; and a display 10 and a display control circuit 11 that display the results processed by the CPU 9.

The air supplying/discharging means 4 includes: a pump 12 that supplies the cuff 3 with air; a pump controller 13 that controls the pump 12 based on an instruction from the CPU 9; an air filter 14 interposed between the sucking inlet of the pump 12 and the atmosphere; a solenoid valve 15 that opens and closes the cuff 3 with respect to the atmosphere; an air filter 16 and a resistor 17 interposed between the solenoid valve 15 and the cuff 3; and a solenoid valve drive unit 18 that controls the solenoid valve 15 based on an instruction from the CPU 9.

The arterial blood oxygen saturation degree measuring section 2 includes: two LEDs 21, 22 that emit rays of light whose wavelengths are different from each other; an LED drive circuit 23 that drives these LEDs; a current control circuit 24 that controls current flowing through the LED drive circuit 23 based on an instruction from the CPU 9; a photodiode 25 that is arranged so as to confront the LEDs 21, 22; and a signal processing circuit 26 that processes an output signal from the photodiode 25 and outputs the processed data to the A/D converter 8 based on an instruction from the CPU 9. The arterial blood oxygen saturation degree measurement section 2 also includes: the CPU 9, the A/D converter 8, the display 10, and the display control circuit 11 that are co-used with the blood pressure measuring section 1.

As described above, this mode of embodiment includes the arterial blood oxygen saturation degree measuring section 2. As a result, the cuff 3, the LEDs 21, 22, and the photodiode 25 are integrated with one another to form a composite sensor 28 that measures both blood pressure and arterial blood oxygen saturation degree. These members are arranged so that when the cuff 3 is wrapped around a finger of a subject, the LEDs 21, 22 inject light onto the finger, and the photodiode 25 receives transmitted light.

Figure 2:
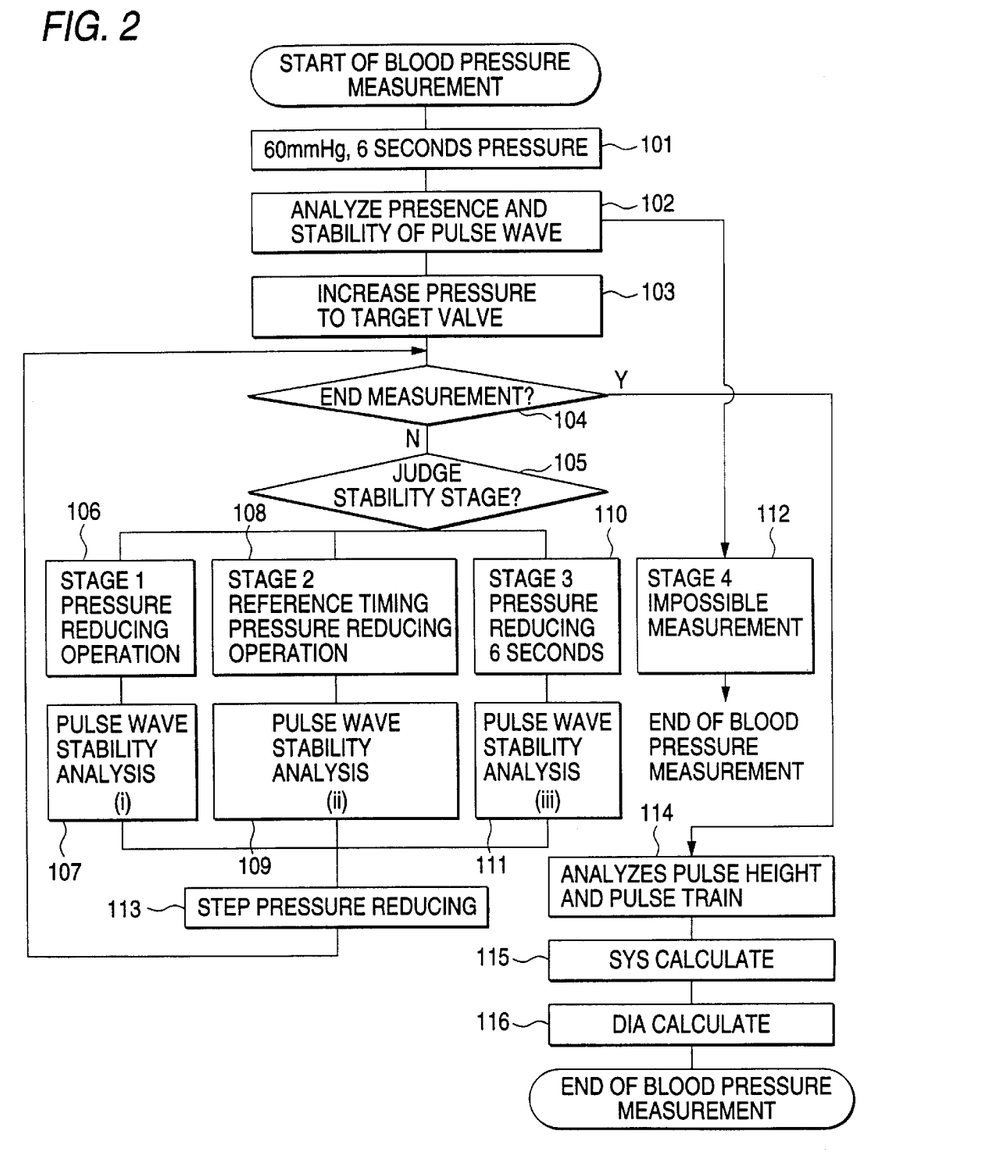
FIG. 2 is a diagram illustrative of an operation of the apparatus shown in FIG. 1.

The CPU 9 executes processing programs for two modes, a blood pressure measuring mode and an arterial blood oxygen saturation degree measuring mode. The flow of the processing program for the blood pressure measuring mode is shown in FIG. 2. In this mode of embodiment, Step 101 shown in FIG. 2 corresponds to the control step with the first cuff pressure control means; Step 102 in FIG. 2 corresponds to the detecting step with the stability detecting means; Step 105 in FIG. 2 corresponds to the judging step with the judging means; Steps 103, 104, 106, 108, 110, 113 in FIG. 2 are operated with the second cuff pressure control means; and Steps 107, 109, 111, 114 to 116 in FIG. 2 are performed with the blood pressure value determining means.

Then, an operation of this mode of embodiment will be described with reference to the flowchart shown in FIG. 2. First, an operator attaches the composite sensor 28 to a finger of a subject, and turns a not shown power switch on. As a result, the CPU 9 is set to the blood pressure measuring mode and controls the air supplying/discharging means 4 to set the cuff pressure to 60 mmHg and maintain this state for 6 seconds (Step 101). That is, the CPU 9 not only drives the solenoid valve drive unit 18 to close the solenoid valve 15, controls the pump controller 13 to drive the pump 12, supplies the cuff 3 with the air introduced from the atmosphere through the air filter 14, but also receives the output of the pressure sensor 5 through the dc amplifier 6 and the A/D converter 8, thereby monitors the cuff pressure, and stops the operation of the pump 12 by controlling the pump controller 13 when the cuff pressure has reached 60 mmHg.

Figure 3:
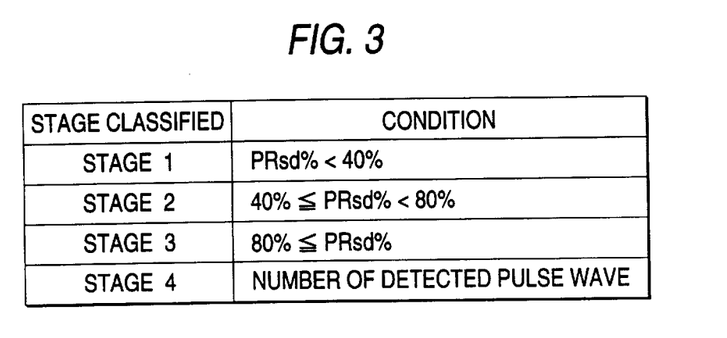
FIG. 3 is a diagram showing a classification of step pressure reducing stages.

Then, the CPU 9 analyzes the presence and stability of pulse waves when the cuff pressure is 60 mmHg (Step 102). That is, the CPU 9 detects pressure pulse waves for 6 seconds from a signal obtained through the pressure sensor 5, the ac amplifier 7, and the A/D converter 8, selects pulse waves that satisfy a predetermined standard from these detected pulse waves, calculates an average pulse wave peak value out of these selected pulse waves, picks up pulse waves that fall within a range of ±20% of the average pulse wave peak value, from all the detected pulse waves, and finds a standard deviation PRsd of the pulse interval PR for these pulse waves. That is, a solution is found for an equation $PRsd=\{\Sigma(PR-PRave)^2(n-1)\}^{1/2}$. In the equation, PRave is the average pulse interval of all the detected pulse waves, and n is the number of pulse waves used in the calculation. The CPU 9 further calculates a normalized standard deviation PRsd % for the average pulse interval PRave. That is, a solution is found for an equation PRsd %=PRsd/PRave*100. The CPU 9 determines a type of step pressure reducing operation, i.e., a step pressure reducing stage based on the calculated PRsd % and stores a stage number in a stage type area of a memory. That is, a step pressure reducing stage is determined by judging which stage in the classified stages shown in FIG. 3 the calculated PRsd % corresponds to. Further, when the power switch of the apparatus has been turned on, the CPU 9 controls the current control circuit 24 to blink the LEDs 21, 22, and receives data on a change in the transmitted light of the lED 21 through the photodiode 25 and the signal processing circuit 26. The CPU 9 then calculates a reference pulse rate from the pulse waves detected by such transmitted light for a period of 6 seconds and stores the calculated reference pulse rate. Now, the CPU 9 first classifies the pulse rates of the light pulse waves, then finds a frequency distribution by the class, and stores the pulse rate obtained from the pulse waves belonging to the class having the highest frequency as the reference pulse rate in a reference pulse rate area of the memory.

Then, the CPU 9 controls the air supplying/discharging means 4 to thereby increase the cuff pressure to an initially set target value for making a regular blood pressure measurement (Step 103). That is, the CPU 9 not only drives the pump 12 by controlling the pump controller 13 and supplies the cuff 3 with the air introduced from the atmosphere through the air filter 14, but also receives the output of the pressure sensor 5 through the dc amplifier 6 and the A/D converter 8, thereby monitors the cuff pressure, and stops the operation of the pump 12 by controlling the pump controller 13 when the cuff pressure has reached the initially set target value.

Then, the CPU 9 judges whether or not the measurement has been ended (Step 104). Here, the CPU 9 judges that the measurement end timing has arrived either when the pulse wave peak value is below a set value or when the cuff pressure is below a set value.

The CPU 9, having judged that the measurement end timing has not yet arrived in Step 104, then identifies the stability stage (Step 105). That is, the CPU 9 selects a stage having a number that is written in the stage type area. Here, having selected stage number 1, the CPU 9 sets a pressure reducing timing so that a single step of pressure reducing operation is started upon appearance of a next pulse wave (Step 106) Then, the CPU 9 does a pulse wave stability analysis (i) (Step 107). Here, the CPU 9 monitors pulse waves obtained from the ac amplifier 7, and writes the content in the stage type area as stage number 2 upon judgment that such pulse waves are out of the range of ±20% of the reference pulse rate.

Further, the CPU 9, having selected stage number 2 in Step 105, sets the pressure reducing timing so that a single step of pressure reducing operation is started (reference pulse rate=3) seconds from the current timing and the pulse waves are detected during the time (Step 108). Then, the CPU 9 does a pulse wave stability analysis (ii) (Step 109). Here, the CPU 9 monitors pulse waves detected by the ac amplifier 7, and judges whether or not a difference between the pulse wave interval and the reference pulse rate as well as a difference in the variations of the amplitudes of the detected pulse waves exceed the maximums of their set ranges. When the CPU 9 judges that these differences exceed the maximums of their set ranges, the CPU writes the content in the stage type area as stage number 3. When the CPU 9 judges that these differences are below the minimums of their set ranges, the CPU 9 not only writes the content in the stage type area as stage number 1, but also updates the content in the reference pulse rate area with the pulse rate of the current pulse waves.

Further, when the CPU 9 selects stage number 3 in Step 105, the CPU 9 sets the pressure reducing timing so that a single step of pressure reducing operation is started 6 seconds from the current timing and the pulse waves are detected during the time (Step 110). Then, the CPU 9 does a pulse wave stability analysis (iii) (Step 111). Here, the CPU 9 monitors pulse waves detected by the ac amplifier 7, calculates PRsd % in a manner similar to Step 102, determines a step pressure reducing stage based on the calculated PRsd %, and writes the content in the stage type area as the determined stage number. In this case, if the CPU 9 writes the content as stage number 2, then the CPU 9 determines the reference pulse rate in a manner similar to Step 102 and updates the content in the reference pulse rate area with the determined reference pulse rate. When any one of the pulse wave stability analyses (i) to (iii) have been ended (Steps 107, 109, 111), the CPU 9 starts a single step of pressure reducing operation at the set timing (Step 113). That is, the CPU 9 controls the solenoid valve controller 18 first to open the solenoid valve 15 and then to close the solenoid valve 15 when the cuff pressure has been reduced by a predetermined quantity. After this processing has been ended, the CPU 9 returns to Step 104.

Further, having selected stage number 4 in Step 102, the CPU 9 judges that measurement cannot be made, and causes the display 10 to indicate to that effect (Step 112). Then, the CPU 9 ends the blood pressure measurement processing.

Having judged that the pulse wave measurement has been ended in Step 104, the CPU 9 then analyzes the pulse height and pulse train of the detected pulse waves (Step 114). That is, the CPU 9 removes noise from the detected pulse waves, determines a single pulse wave per step pressure, and calculates respective pulse wave peak values. For stage number 1, the peak value of a single pulse wave appearing within ±20% of the reference pulse rate is calculated with other component removed as noise; for stage number 2, an average of the peak values of a plurality of pulse waves appearing is calculated; and for stage number 3, an average of the peak values of a plurality of pulse waves appearing within a predetermined range is calculated with other peak values either greater or smaller than the values within the predetermined range removed.

Then, the CPU 9 calculates a systolic blood pressure by referring to the pulse height and pulse train of the pulse waves calculated in Step 114 (Step 115), and then calculates a diastolic blood pressure by referring to the pulse height and pulse train of the pulse waves calculated in Step 114. It may be noted that these calculated blood pressure values are displayed on the display 10. Upon end of the blood pressure measurement processing, the CPU 9 executes the processing of arterial blood oxygen saturation degree measurement in the arterial blood oxygen saturation degree measuring mode. Since this mode of embodiment is principally directed Lo the blood pressure measurement processing, a description of the arterial blood oxygen saturation degree measurement processing will be omitted.

Figure 4:
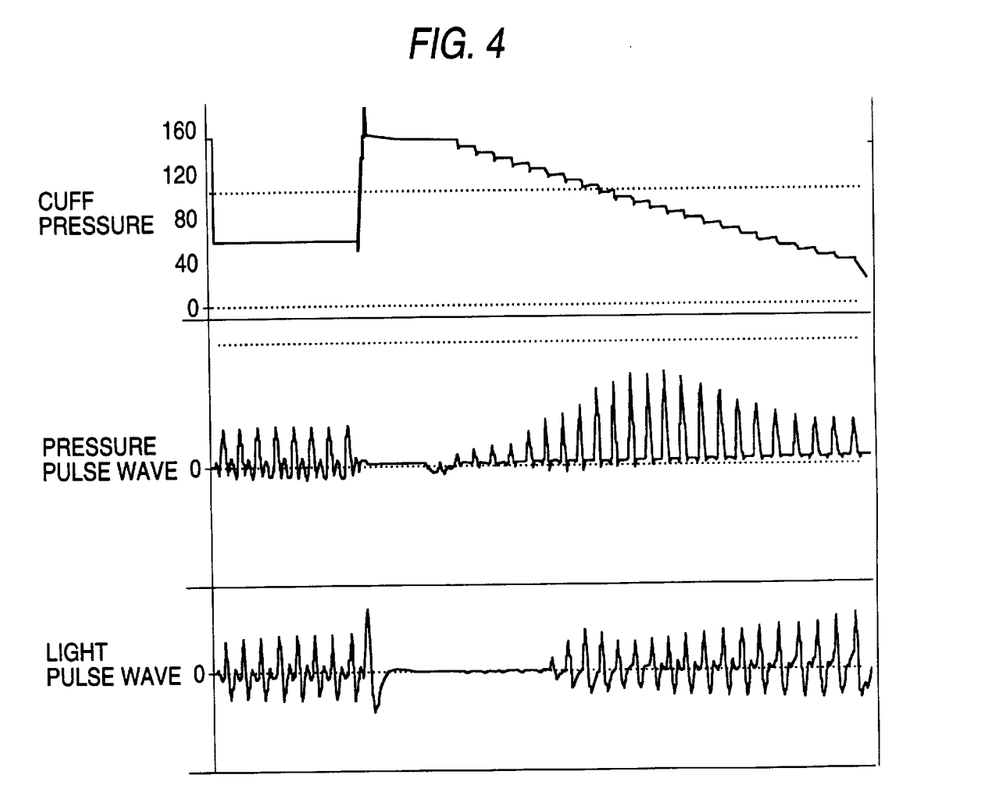
FIG. 4 is a diagram showing an example of a measurement result obtained by the apparatus shown in FIG. 1.

FIG. 4 shows an example of a measurement result obtained using the apparatus, which is this mode of embodiment of the invention. This is an example in which the step pressure reducing operation according to stage number 1 was performed.

This mode of embodiment is provided as analyzing, during measurement, the degree of stability of a pulse wave detected for regular blood pressure measurement, and changing the step pressure reducing stage in accordance with the measurement result. That is, when pulse waves become more erratic, a larger number of pulse wave data are gathered by increasing the single step pressure reducing time period, and when pulse waves become less erratic, only a smaller number of pulse wave data are gathered by decreasing the single step pressure reducing time period. Therefore, an extremely correct measurement can be made within a short period of time.

In this mode of embodiment, the reference pulse rate is detected from an electrical signal by driving the arterial blood oxygen saturation degree measuring section 2 during the processing of Step 102 in FIG. 2, the electrical signal corresponding to any one of transmitted rays of flight out of two rays of light whose wavelengths are different, and the two rays of light being injected onto a finger of a subject. The reference pulse rate may be detected using pulse waves derived from the pressure of the air within the cuff. However, since pulse waves derived from light are less affected by vibration, pulse waves derived from light allow a correct measurement result to be obtained.

Further, while the cuff pressure is reduced by step pressure reducing method, the cuff pressure may be reduced by continuous pressure reducing method. That is, a single step duration is set for each stage number in Steps 106, 108, 110 shown in FIG. 2. Instead of these Steps, defined is a step that sets not only a pressure reducing speed (e.g., a slower speed with larger stage number) for each stage number, but also an elapsed time corresponding to the single step duration of each of those Steps. Further, a single step of pressure reducing operation is implemented every time a set time period has elapsed in Step 113 in FIG. 2. Instead of Step 113, defined is a step that starts continuous pressure reducing operation corresponding to the set pressure reducing speed (the pressure reducing operation is continued once started, and the pressure reducing speed and the elapsed time corresponding to the single step duration of each of the Steps are changed in the continuous pressure reducing operation). Still further, while a single pulse wave is determined per single step pressure in Step 114 in FIG. 2. Instead of Step 114, defined is a step that calculates an average of the peak values of pulse waves appearing within a predetermined range around the reference pulse rate. As a result of this method, a larger number of pulse waves can be measured under continuous slow pressure reducing operation when the pulse waves are greatly erratic, whereas a smaller number of pulse waves can be measured under rapid pressure reducing operation when the pulse waves are less erratic. This method can also provide a correct measurement result in a manner similar to the aforementioned mode of embodiment.

According to the present invention, blood pressure measurement is made after calculating the degree of stability of detected pulse waves and performing a predetermined pressure reducing operation when the calculated degree exceeds a certain level. Therefore, the measurement result is correct, and a highly reliable result can be obtained even if the measurement is made in a vibrating motor vehicle.

According to the present invention, the degree of stability of detected pulse waves is calculated before blood pressure measurement, and a predetermined pressure reducing operation corresponding to the calculated degree is performed during the blood pressure measurement. That is, when pulse waves are greatly erratic, a larger number of pulse wave data are gathered by increasing the pressure reducing operation time period, whereas when pulse waves are less erratic, a smaller number of pulse wave data are gathered by decreasing the pressure reducing operation time period. Therefore, an extremely correct measurement can be made within a short period of time.

According to the present invention, the degree of stability of detected pulse waves is calculated before blood pressure measurement, and a type of predetermined pressure reducing operation corresponding to the calculated degree is performed for the initial stage of the blood pressure measurement, and the degree of stability of pulse waves is calculated also during the blood pressure measurement, and the type of predetermined pressure reducing operation is changed so as to correspond to the re-calculated degree. Therefore, a more correct measurement can be made within a short period of time.

According to the present invention, the cuff pressure can be maintained at a predetermined level during measurement since a predetermined pressure reducing operation is a step pressure reducing operation. Therefore, a more correct measurement can be made.

What is claimed is:

1. A noninvasive blood pressure measuring device comprising:

a cuff for measuring blood pressure based on a pressure of gas within said cuff, said cuff to be wrapped around a body;

gas supplying/discharging means for supplying and discharging said gas within respect to said cuff;

first cuff pressure control means for controlling said gas supplying/discharging means so that said pressure of said gas within said cuff reaches a first pressure;

pulse wave detecting means for detecting a pulse wave in said pressure while said pressure of said gas within said cuff is maintained at said first pressure;

stability detecting means for detecting a degree of stability of said pulse wave;

pressure reducing means for performing a predetermined step pressure reducing operation, selected from a plurality of predetermined step pressure reducing operations, to said gas within said cuff;

judging means for selecting said predetermined step pressure reducing operation from said plurality of predetermined step pressure reducing operations in accordance with said degree of stability of said pulse wave detected by said stability detecting means;

second cuff pressure control means for controlling said gas supplying/discharging means to increase said pressure of said gas within said cuff to a second pressure, and for performing said predetermined s pressure reducing operation, selected by said judging means, to said pressure of said gas within said cuff; and blood pressure value determining means for detecting a pulse wave in said pressure while said predetermined step pressure reducing operation is performed to said pressure of said gas within said cuff by said second cuff pressure control means for determining a blood pressure value based on said pulse wave.

2. The noninvasive blood pressure measuring device according to claim 1, wherein said pulse wave detecting means comprises:

light emitting means for irradiating a living tissue; and light receiving means for receiving light irradiated from said light emitting means and for obtaining an electrical signal of a pulse wave.

3. A noninvasive blood pressure measuring device comprising:

a cuff for measuring blood pressure based on a pressure of gas within said cuff, said cuff to be wrapped around a body;

gas supplying/discharging means for supplying and discharging said gas within respect to said cuff;

first cuff pressure control means for controlling said gas supplying/discharging means so that said pressure of said gas within said cuff reaches a first pressure;

pulse wave detecting means for detecting a pulse wave in said pressure while said pressure of said gas within said cuff is maintained at said first pressure;

stability detecting means for detecting a degree of stability of said pulse wave;

pressure reducing means for performing a first predetermined step pressure reducing operation, selected from a plurality of predetermined step pressure reducing operations, to said gas within said cuff;

judging means for selecting said first predetermined step pressure reducing operation from said plurality of predetermined step pressure reducing operations in accordance with said degree of stability detected by said stability detecting means;

stability analyzing means for analyzing a degree of stability of said pulse wave detected by said pulse wave detecting means while any one of said plurality of predetermined step pressure reducing operations is performed, and for selecting a second predetermined step pressure reducing operation from said plurality of predetermined s pressure reducing operations based on an analyzed degree of stability;

second cuff pressure control means for controlling said gas supplying/discharging means to increase said pressure of said gas within said cuff to a second pressure, for performing said first predetermined step pressure reducing operation selected by said judging means to said pressure of said gas within said cuff and for controlling said gas supplying/discharging means so that said second predetermined step pressure reducing operation selected by said stability analyzing means is performed to said pressure of said gas within said cuff thereafter; and blood pressure value determining means for detecting a pulse wave in said pressure while said first and second predetermined step pressure reducing operations are performed to said pressure of said gas within said cuff by said second cuff pressure control means for determining a blood pressure value based on said pulse wave.

4. The noninvasive blood pressure measuring device according to claim 3, wherein said pulse wave detecting means comprises:

light emitting means for irradiating a living tissue; and light receiving means for receiving light irradiated from said light emitting means and for obtaining an electrical signal of a pulse wave.

5. A noninvasive blood pressure method comprising the steps of:

supplying gas to a cuff so that a pressure of said gas within said cuff reaches a first pressure;

detecting a pulse wave in said pressure while said pressure of said gas within said cuff is maintained at said first pressure;

detecting a degree of stability of said pulse wave;

selecting a predetermined step pressure reducing operation from a plurality of predetermined step pressure reducing operations in accordance with said degree of stability;

increasing said pressure of said gas in said cuff to a second pressure;

performing said predetermined step pressure reducing operation;

detecting a pulse wave in said pressure while said predetermined step pressure reducing operation is performed to said pressure of said gas within said cuff; and determining a blood pressure value based on said pulse wave.

6. A noninvasive blood pressure method comprising the steps of:

supplying gas to a cuff so that a pressure of said gas within said cuff reaches a first pressure;

detecting a pulse wave in said pressure while said pressure of said gas within said cuff is maintained at said first pressure;

detecting a degree of stability of said pulse wave;

selecting a first predetermined step pressure reducing operation from a plurality of predetermined step pressure reducing operations in accordance with said degree of stability;

analyzing a degree of stability of a pulse wave in said pressure of said gas within said cuff while any one of said plurality of predetermined step pressure reducing operations is performed, and for selecting a second predetermined step pressure reducing operation from said plurality of predetermined step pressure reducing operations based on an analyzed degree of stability;

increasing said pressure of said gas in said cuff to a second pressure;

performing said first predetermined pressure reducing operation to said pressure of said gas within said cuff;

performing said second predetermined step pressure reducing operation to said pressure of said gas within said cuff thereafter;

detecting a pulse wave in said pressure while said first and second predetermined step pressure reducing operations are performed to said pressure of said gas within said cuff; and determining a blood pressure value based on said pulse wave.

7. A noninvasive blood pressure measuring device comprising:

a cuff; to be wrapped around a body, for measuring blood pressure based on a pressure of gas within said cuff;

gas supplying/discharging means for supplying and discharging said gas with respect to said cuff;

first cuff pressure control means for controlling said gas supplying/discharging means so that said pressure of said gas within said cuff reaches a first pressure;

pulse wave detecting means for detecting a pulse wave in said pressure while said pressure of said gas within said cuff is maintained at said first pressure by said first cuff pressure control means;

stability detecting means for detecting a degree of stability of said pulse wave;

pressure reducing means for performing a predetermined continuous pressure reducing operation, selected from a plurality of predetermined continuous pressure reducing operations, to said gas within said cuff;

judging means for selecting said predetermined continuous pressure reducing operation from said plurality of predetermined continuous pressure reducing operations in accordance with said degree of stability of said pulse wave detected by said stability detecting means;

second cuff pressure control means for controlling sad gas supplying/discharging means to increase said pressure of said gas within said cuff to a second pressure, and for performing said predetermined continuous pressure reducing operation, selected by said judging means, to said pressure of said gas within said cuff; and blood pressure value determining means for detecting a pulse wave in said pressure while said predetermined continuous pressure reducing operation is performed to said pressure of said gas within said cuff, by said second cuff pressure control means, for determining a blood pressure value based on a detected pulse wave.

8. The noninvasive blood pressure measuring device according to claim 7, wherein a pressure reducing speed of said predetermined continuous pressure reducing operation is slow when said stability of said pulse wave is low.

9. The noninvasive blood pressure measuring device according to claim 7, wherein said pulse wave detecting means comprises:

light emitting means for irradiating a living tissue; and light receiving means for receiving light irradiated from said light emitting means and for obtaining an electrical signal of pulse wave.

10. A noninvasive blood pressure measuring device comprising:

a cuff, to be wrapped around a body, for measuring blood pressure based on a pressure of gas within said cuff;

gas supplying/discharging means for supplying and discharging said gas with respect to said cuff;

first cuff pressure control means for controlling said gas supplying/discharging means so that said pressure of said gas within said cuff reaches a first pressure;

pulse wave detecting means for detecting a pulse wave in said pressure while said pressure of said gas within said cuff is maintained at said first pressure by said first cuff pressure control means;

stability detecting means for detecting a degree of stability of said pulse wave;

pressure reducing means for performing a first predetermined continuous pressure reducing operation, selected from a plurality of predetermined continuous pressure reducing operations, to said gas within said cuff;

judging means for selecting said first predetermined continuous pressure reducing operation from said plurality of predetermined continuous pressure reducing operations in accordance with said degree of stability of said pulse wave detected by said stability detecting means;

stability analyzing means for analyzing a degree of stability of said pulse wave detected by said pulse wave detecting means while any one of said plurality of predetermined continuous pressure reducing operations from said plurality of predetermined continuous pressure reducing operations is performed based on said degree of stability; and for selecting a second predetermined continuous pressure reducing operation based on an analyzed degree of stability;

second cuff pressure control means for controlling said gas supplying/discharging means so that after said pressure of said gas within said cuff has increased to a second pressure, said first predetermined continuous pressure reducing operation, selected by said judging means, is performed, and for controlling said gas supplying/discharging means so that said second predetermined continuous pressure reducing operation selected by said stability analyzing means is performed to said pressure of said gas within said cuff thereafter; and blood pressure value determining means for detecting a pulse wave in said pressure while said first and second predetermined continuous pressure reducing operations are performed to said pressure of said gas within said cuff, by said second cuff pressure control means, for determining a blood pressure value based on said pulse wave.

11. The noninvasive blood pressure measuring device according to claim 10, wherein a pressure reducing speed of said predetermined continuous pressure reducing operation is slow when said stability of said pulse wave is low.

12. The noninvasive blood pressure measuring device according to claim 10, wherein said pulse wave detecting means comprises:

light emitting means for irradiating a living tissue; and light receiving means for receiving light irradiated from said light emitting means and for obtaining an electrical signal of pulse wave.

13. A noninvasive blood pressure method comprising the steps of:

supplying gas to a cuff so that said cuff reaches a first pressure;

detecting a pulse wave of said pressure while said pressure of said gas within said cuff is maintained at said first pressure;

detecting a degree of stability of said pulse wave;

selecting a predetermined continuous pressure reducing operation, from a plurality of predetermined continuous pressure reducing operations, in accordance with said degree of stability;

increasing said pressure of said gas in said cuff to a second pressure;

performing said predetermined continuous pressure reducing operation, selected by said judging means, after said second pressure is reached;

detecting a pulse wave in said pressure while said predetermined continuous pressure reducing operation is performed; and determining a blood pressure value based on said pulse wave detected in said pressure.

14. The noninvasive blood pressure method according to claim 13, wherein a pressure reducing speed of said predetermined continuous pressure reducing operation is slow when the stability of said pulse wave is low.

15. A noninvasive blood pressure method comprising the steps of:

supplying gas to a cuff so that said cuff reaches a first pressure;

detecting a pulse wave in said pressure while said pressure of said gas within said cuff is maintained at said first pressure;

detecting a degree of stability of said pulse wave;

selecting a first predetermined continuous pressure reducing operation from a plurality of predetermined continuous pressure reducing operations in accordance with said degree of stability;

analyzing a degree of stability of a pulse wave detected by using said pulse wave detecting means while any one of said plurality of predetermined continuous pressure reducing operations is performed;

selecting a second predetermined continuous pressure reducing operation from said plurality of predetermined continuous pressure reducing operations based on an analyzed degree of stability;

increasing said pressure in said cuff to a second pressure;

performing said first predetermined continuous pressure reducing operation;

performing said second predetermined continuous pressure reducing operation;

detecting a pulse wave in said pressure while said first and second predetermined continuous pressure reducing operations are performed to said pressure of said gas within said cuff; and determining a blood pressure value based on said pulse wave.

16. The noninvasive blood pressure method according to claim 15, wherein a pressure reducing speed of said predetermined continuous pressure reducing operation is slow when the stability of said pulse wave is low.

17. A noninvasive blood pressure measuring device comprising:

a cuff, to be wrapped around a body, for measuring blood pressure based on a pressure of gas within said cuff;

gas supplying/discharging means for supplying and discharging said gas with respect to said cuff;

first cuff pressure control means for controlling said gas supplying/discharging means so that said pressure of said gas within said cuff reaches a predetermined pressure;

pulse wave detecting means for detecting a pulse wave in said gas while said pressure of said gas within said cuff is maintained at said predetermined pressure;

stability detecting means for detecting a degree of stability of said pulse wave;

pressure reducing means for performing a predetermined step pressure reducing operation, selected from a plurality of predetermined step pressure reducing operations, to said gas within said cuff;

judging means for selecting said predetermined step pressure reducing operation from said plurality of predetermined step pressure reducing operations in accordance with said degree of stability of said pulse wave detected by said stability detecting means;

second cuff pressure control means for controlling said gas supplying/discharging means so that said predetermined step pressure reducing operation, selected by said judging means, is performed to said pressure of said gas within said cuff; and blood pressure value determining means for detecting a pulse wave in said pressure while said predetermined step pressure reducing operation is performed to said pressure of said gas within said cuff, by said second cuff pressure control means, for determining a blood pressure value based on a detected pulse wave.

18. The noninvasive blood pressure measuring device according to claim 17, wherein said pulse wave detecting means comprises:

light emitting means for irradiating a living tissue; and light receiving means for receiving light irradiated from said light emitting means and for obtaining an electrical signal of a pulse wave.

19. A noninvasive blood pressure measuring device comprising:

a cuff, to be wrapped around a body, for measuring blood pressure based on a pressure of gas within said cuff;

gas supplying/discharging means for supplying and discharging said gas with respect to said cuff;

first cuff pressure control means for controlling said gas supplying/discharging means so that said pressure of said gas within said cuff reaches a first pressure;

pulse wave detecting means for detecting a pulse wave in said pressure while said pressure of said gas within said cuff is maintained at said first pressure;

stability detecting means for detecting a degree of stability of said detected pulse wave;

pressure reducing means for performing a first predetermined step pressure reducing operation, selected from a plurality of predetermined step pressure reducing operations, to said gas within said cuff;

judging means for selecting said first predetermined step pressure reducing operation from said plurality of predetermined step pressure reducing operations in accordance with said degree of stability of said pulse wave detected by said stability detecting means;

stability analyzing means for analyzing a degree of stability of a pulse wave detected by pulse wave detecting means while any one of said plurality of predetermined step pressure reducing operations, from said plurality of predetermined step pressure reducing operations, based on said degree of stability, and for selecting a second predetermined step pressure reducing operation based on an analyzed degree of stability;

second cuff pressure control means for controlling said gas supplying/discharging means so that said first predetermined step pressure reducing operation, selected by said judging means, is performed to said pressure of said gas within said cuff and for controlling said gas supplying/discharging means so that said second predetermined step pressure reducing operation selected by said stability analyzing means is performed to said pressure of said gas within said cuff thereafter; and blood pressure value determining means for detecting a pulse wave in said pressure while said first and second predetermined step pressure reducing operations are performed to said pressure of said gas within said cuff by said second cuff pressure control means for determining a blood pressure value based on said pulse wave.

20. The noninvasive blood pressure measuring device according to claim 19, wherein said pulse wave detecting means comprises:

light emitting means for irradiating a living tissue; and light receiving means for receiving light irradiated from said light emitting means and for obtaining an electrical signal of a pulse wave.

21. A noninvasive blood pressure measuring device comprising:

a cuff, to be wrapped around a body, for measuring blood pressure based on a pressure of gas within said cuff;

gas supplying/discharging means for supplying and discharging said gas with respect to said cuff;

first cuff pressure control means for controlling said gas supplying/discharging means so that said pressure of said gas within said cuff reaches a first predetermined pressure;

pulse wave detecting means for detecting a pulse wave while said pressure of said gas within said cuff is maintained at said first predetermined pressure;

stability detecting means for detecting a degree of stability of said pulse wave;

pressure reducing means for performing a predetermined continuous pressure reducing operation, selected from a plurality of predetermined continuous pressure reducing operations, to said gas within said cuff;

judging means for selecting said predetermined continuous pressure reducing operation from said plurality of predetermined continuous pressure reducing operations in accordance with said degree of stability of said pulse wave detected by said stability detecting means;

second cuff pressure control means for controlling said gas supplying/discharging means so that said predetermined continuous pressure reducing operation, selected by said judging means, is performed to said pressure of said gas within said cuff; and blood pressure value determining means for detecting a pulse wave in said pressure while said predetermined continuous pressure reducing operation is performed to said pressure of said gas within said cuff, by said second cuff pressure control means, for determining a blood pressure value based on said pulse wave.

22. The noninvasive blood pressure measuring device according to claim 21, wherein a pressure reducing speed of said predetermined continuous pressure reducing operation is slow when said stability of said pulse wave is low.

23. The noninvasive blood pressure measuring device according to claim 21, wherein said pulse wave detecting means comprises:

light emitting means for irradiating a living tissue; and light receiving means for receiving light irradiated from said light emitting means and for obtaining an electrical signal of a pulse wave.

24. A noninvasive blood pressure measuring device comprising:

a cuff to be wrapped around a body, for measuring blood pressure based on a pressure of gas within said cuff;

gas supplying/discharging means for supplying and discharging said gas with respect to said cuff;

first cuff pressure control means for controlling said gas supplying/discharging means so that said pressure of said gas within said cuff reaches a first predetermined pressure;

pulse wave detecting means for detecting a pulse wave while said pressure of said gas within said cuff is maintained at said first predetermined pressure;

stability detecting means for detecting a degree of stability of said pulse wave;

judging means for selecting a first predetermined continuous pressure reducing operation from a plurality of predetermined continuous pressure reducing operations in accordance with said degree of stability of said pulse wave detected by said stability detecting means;

pressure reducing means for performing said first predetermined continuous pressure reducing operation, selected from said plurality of predetermined continuous pressure reducing operations, to said gas within said cuff;

stability analyzing means for analyzing a degree of stability of a pulse wave detected by using said pulse wave detecting means while any one of said plurality of predetermined continuous pressure reducing operations is performed based on said degree of stability, and for selecting a second predetermined continuous pressure reducing operation based upon an analyzed degree of stability;

second cuff pressure control means for controlling said gas supplying/discharging means so that said first predetermined continuous pressure reducing operation, selected by said judging means, is performed to said pressure of said gas within said cuff, and for controlling said gas supplying/discharging means so that said second predetermined continuous pressure reducing operation selected by said stability analyzing means is performed to said pressure of said gas within said cuff thereafter; and blood pressure value determining means for detecting a pulse wave in said pressure while said first and second predetermined continuous pressure reducing operations are performed to said pressure of said gas within said cuff by said second cuff pressure control means for determining a blood pressure value based on said pulse wave.

25. The noninvasive blood pressure measuring device according to claim 24, wherein a pressure reducing speed of said predetermined continuous pressure reducing operation is slow when said stability of said pulse wave is low.

26. The noninvasive blood pressure measuring device according to claim 24, wherein said pulse wave detecting means comprises:

light emitting means for irradiating a living tissue; and light receiving means for receiving light irradiated from said light emitting means and for obtaining an electrical signal of a pulse wave.

27. A noninvasive blood pressure method comprising the steps of:

supplying gas to a cuff so that said cuff reaches a predetermined pressure;

detecting a pulse wave in a pressure of said gas in said cuff while said pressure of said gas within said cuff is maintained at said predetermined pressure;

detecting a degree of stability of said pulse wave;

selecting a predetermined step pressure reducing operation from a plurality of predetermined step pressure reducing operations in accordance with a detected degree of stability;

controlling said gas supplying/discharging means so that said predetermined step pressure reducing operation, selected by said judging means, is performed to said pressure of said gas within said cuff;

detecting a pulse wave in said pressure while said predetermined step pressure reducing operation is performed to said pressure of said gas within said cuff; and determining a blood pressure value based on said pulse wave detected in said pressure.

28. A noninvasive blood pressure method comprising the steps of:

supplying gas to a cuff so that said cuff reaches a predetermined pressure;

detecting a pulse wave of a pressure of said gas while said pressure of said gas within said cuff is maintained at said predetermined pressure;

detecting a degree of stability of said pulse wave;

selecting a first predetermined step pressure reducing operation from a plurality of predetermined step pressure reducing operations in accordance with a detected degree of stability;

analyzing a degree of stability of a pulse wave detected by using said pulse wave detecting means while any one of said plurality of predetermined step pressure reducing operations is performed, and for selecting a second predetermined step pressure reducing operation from said plurality of predetermined step pressure reducing operations based on an analyzed degree of stability;

performing said first predetermined step pressure reducing operation;

performing said second predetermined step pressure reducing operation to said pressure of said gas within said cuff;

detecting a pulse wave in said pressure while said first and second predetermined step pressure reducing operations are performed to said pressure of said gas within said cuff; and determining a blood pressure value based on said pulse wave detected in said pressure.

29. A noninvasive blood pressure method comprising the steps of:

supplying gas to a cuff so that said cuff reaches a predetermined pressure;

detecting a pulse wave in a pressure of said gas while said pressure of said gas within said cuff is maintained at said predetermined pressure;

detecting a degree of stability of said pulse wave;

selecting a predetermined continuous pressure reducing operation from a plurality of predetermined continuous pressure reducing operations in accordance with a detected degree of stability;

performing said predetermined continuous pressure reducing operation of said pressure of said gas within said cuff;

detecting a pulse wave in said pressure while said predetermined continuous pressure reducing operation is performed; and determining a blood pressure value based on said pulse wave detected in said pressure.

30. The noninvasive blood pressure method according to claim 29, wherein a pressure reducing speed of said predetermined continuous pressure reducing operation is slow when said stability of said pulse wave is low.

31. A noninvasive blood pressure method comprising the steps of:

supplying gas to a cuff so that said cuff reaches a predetermined pressure;

detecting a pulse wave of a pressure of said gas while said pressure of said gas within said cuff is maintained at said predetermined pressure;

detecting a degree of stability of said pulse wave;

selecting a first predetermined continuous pressure reducing operation from a plurality of predetermined continuous pressure reducing operations in accordance with a detected degree of stability;

analyzing a degree of stability of a pulse wave detected by using said pulse wave detecting means while any one of said plurality of predetermined continuous pressure reducing operations is performed, and for selecting a second predetermined continuous pressure reducing operation from said plurality of predetermined continuous pressure reducing operations based on an analyzed degree of stability;

performing said first predetermined continuous pressure reducing operations;

performing said second predetermined continuous pressure reducing operation of said gas within said cuff;

detecting a pulse wave in said pressure while said first and second predetermined continuous pressure reducing operations are performed to said pressure of said gas within said cuff; and determining a blood pressure value based on said pulse wave detected in said pressure.

32. The noninvasive blood pressure method according to claim 31, wherein a pressure reducing speed of said predetermined continuous pressure reducing operation is slow when said stability of said pulse wave is low.

* * * * *